US006203493B1

(12) United States Patent
Ben-Haim (10) Patent No.: US 6,203,493 B1
(45) Date of Patent: Mar. 20, 2001

(54) ATTACHMENT WITH ONE OR MORE SENSORS FOR PRECISE POSITION DETERMINATION OF ENDOSCOPES

(75) Inventor: Shlomo Ben-Haim, Haifa (IL)

(73) Assignee: Biosense, Inc., New Brusnwick, NJ (US)

( * ) Notice: Subject to any disclaimer, the term of this patent is extended or adjusted under 35 U.S.C. 154(b) by 0 days.

(21) Appl. No.: 09/117,792

(22) PCT Filed: Feb. 14, 1997

(86) PCT No.: PCT/IL97/00061

§ 371 Date: Oct. 18, 1999

§ 102(e) Date: Oct. 18, 1999

(87) PCT Pub. No.: WO97/29679

PCT Pub. Date: Aug. 21, 1997

Related U.S. Application Data (60) Provisional application No. 60/011,743, filed on Feb. 15, 1996, and provisional application No. 60/012,242, filed on Feb. 26, 1996.

(30) Foreign Application Priority Data

| Feb. 15, 1996 | (IL) | ......................................... 117148 |
| Sep. 17, 1996 | (IL) | ......................................... 119262 |

(51) Int. Cl.[7] ......................................................... A61B 1/00
(52) U.S. Cl. ........................... 600/117; 600/145; 600/424
(58) Field of Search .................................. 600/117, 114, 600/407, 409, 424; 128/899

(56) References Cited

U.S. PATENT DOCUMENTS

| 3,644,825 | 2/1972 | Davis, Jr. et al. . |
| 3,868,565 | 2/1975 | Kuipers . |
| 3,913,565 | * 10/1975 | Kawahara ............................ 600/114 |
| 4,017,858 | 4/1977 | Kuipers . |
| 4,054,881 | 10/1977 | Raab . |
| 4,560,930 | 12/1985 | Kouno . |
| 4,570,354 | 2/1986 | Hindes . |

(List continued on next page.)

FOREIGN PATENT DOCUMENTS

| WO 94/00050 | 1/1994 | (WO) . |
| WO 94/04938 | 3/1994 | (WO) . |
| WO 94/06349 | 3/1994 | (WO) . |
| WO 94/23647 | 10/1994 | (WO) . |
| WO 94/28782 | 12/1994 | (WO) . |
| WO 95/05773 | 3/1995 | (WO) . |

(List continued on next page.)

OTHER PUBLICATIONS

"Effects of laser irradiation delivered by flexible fiberoptic system on the left ventricular internal myocardium" American Heart Journal, Sep. 1983, pp. 587–590.

Dorothy Bonn, "High–Power laser help the Ischaemic Heart", The Lancet, vol. 348 (Jul. 13, 1996) p. 118.

Mahmood Mirhoseini et al. "Transmyocardial Laser Revascularization: A Review" Journal of Clinical Laser Medicine & Surgery. vol. 11(1993) pp. 15–19.

Mahmood Mirhoseini et al. "Transmyocardial Laser Revascularization: A Review" Journal of Clinical Laser Medicine & Surgery. vol. 11(1993) pp. 15–19.

*Primary Examiner*—John P. Leubecker
(74) *Attorney, Agent, or Firm*—Louis J. Capezzuto (57) ABSTRACT

A locatable endoscope (14) attachment including an attachment (20) connectable to an insertion tube portion of an endoscope for determining the endoscope's (14) position; and one or more sensors (22), fixedly positioned with respect to the attachment (20), which are used for determining the positions of the one or more sensors (22). Preferably, when the attachment (20) is fixedly attached to the endoscope (14), the one or more sensors (22) are distanced from elements of the endoscope which interfere with determining the positions of the one or more sensors (22).

4 Claims, 4 Drawing Sheets

U.S. PATENT DOCUMENTS

| | | |
|---|---|---|
| 4,592,356 | 6/1986 | Gutierrez . |
| 4,613,866 | 9/1986 | Blood . |
| 4,642,786 | 2/1987 | Hansen . |
| 4,651,436 | 3/1987 | Gaal . |
| 4,710,708 | 12/1987 | Rorden et al. . |
| 4,788,987 | 12/1988 | Nickel . |
| 4,849,692 | 7/1989 | Blood . |
| 4,869,238 | 9/1989 | Opie et al. . |
| 4,905,698 | 3/1990 | Strohl, Jr. et al. . |
| 4,917,095 | 4/1990 | Fry et al. . |
| 4,921,482 | 5/1990 | Hammerslag et al. . |
| 4,931,059 | 6/1990 | Markham . |
| 4,945,305 | 7/1990 | Blood . |
| 5,002,137 | 3/1991 | Dickinson et al. . |
| 5,042,486 | 8/1991 | Pfeiler et al. . |
| 5,059,197 | 10/1991 | Urie et al. . |
| 5,078,144 | 1/1992 | Sekino et al. . |
| 5,099,845 | 3/1992 | Besz et al. . |
| 5,125,924 | 6/1992 | Rudko . |
| 5,125,926 | 6/1992 | Rudko et al. . |
| 5,158,084 | 10/1992 | Ghiatas . |
| 5,172,056 | 12/1992 | Voision . |
| 5,195,540 | 3/1993 | Shiber . |
| 5,195,968 | 3/1993 | Lundquist et al. . |
| 5,197,482 | 3/1993 | Rank et al. . |
| 5,211,165 | 5/1993 | Dumoulin et al. . |
| 5,215,680 | 6/1993 | D'Arrigo . |
| 5,217,484 | 6/1993 | Marks . |
| 5,234,426 | 8/1993 | Rank et al. . |
| 5,251,635 | 10/1993 | Dumoulin et al. . |
| 5,253,647 | 10/1993 | Takahashi et al. . |
| 5,255,680 | 10/1993 | Darrow et al. . |
| 5,265,610 | 11/1993 | Darrow et al. . |
| 5,267,960 | 12/1993 | Hayman et al. . |
| 5,273,025 | 12/1993 | Sakiyama et al. . |
| 5,275,166 | 1/1994 | Vaitekunas et al. . |
| 5,295,484 | 3/1994 | Marcus et al. . |
| 5,295,486 | 3/1994 | Wollschager et al. . |
| 5,301,682 | 4/1994 | Debbas . |
| 5,309,913 | 5/1994 | Kormos et al. . |
| 5,325,873 | 7/1994 | Hirschi et al. . |
| 5,368,564 | 11/1994 | Savage . |
| 5,368,592 | 11/1994 | Stern et al. . |
| 5,373,849 | 12/1994 | Maroney et al. . |
| 5,375,596 | 12/1994 | Twiss et al. . |
| 5,377,678 | 1/1995 | Dumoulin et al. . |
| 5,380,316 | 1/1995 | Aita et al. . |
| 5,383,454 | 1/1995 | Bucholz . |
| 5,383,874 | 1/1995 | Jackson et al. . |
| 5,383,923 | 1/1995 | Webster, Jr. . |
| 5,385,148 | 1/1995 | Lesh et al. . |
| 5,389,096 | 2/1995 | Aita et al. . |
| 5,391,199 | 2/1995 | Ben Haim . |
| 5,403,356 | 4/1995 | Hill et al. . |
| 5,404,297 | 4/1995 | Birk et al. . |
| 5,409,004 | 4/1995 | Sloan . |
| 5,423,321 | 6/1995 | Fontenot . |
| 5,425,367 | 6/1995 | Shapiro et al. . |
| 5,425,382 | 6/1995 | Golden et al. . |
| 5,429,132 | 7/1995 | Guy et al. . |
| 5,431,168 | 7/1995 | Webster, Jr. . |
| 5,433,198 | 7/1995 | Desai . |
| 5,437,277 | 8/1995 | Dumoulin et al. . |
| 5,443,489 | 8/1995 | Ben-Haim . |
| 5,450,846 | 9/1995 | Goldreyer . |
| 5,465,717 | 11/1995 | Imran et al. . |
| 5,471,982 | 12/1995 | Edwards et al. . |
| 5,471,988 | 12/1995 | Fujio et al. . |
| 5,480,422 | 1/1996 | Ben-Haim . |
| 5,483,951 | 1/1996 | Frassica et al. . |
| 5,487,391 | 1/1996 | Panescu . |
| 5,538,008 | 7/1996 | Crowe . |
| 5,554,152 | 9/1996 | Aita et al. . |
| 5,555,883 | 9/1996 | Avitall . |
| 5,558,091 | 9/1996 | Acker et al. . |
| 5,558,092 | 9/1996 | Unger et al. . |
| 5,577,502 | 11/1996 | Darrow et al. . |
| 5,588,432 | 12/1996 | Crowley . |
| 5,617,857 | 4/1997 | Chader et al. . |
| 5,622,169 | 4/1997 | Golden et al. . |
| 5,715,822 | 2/1998 | Watkins et al. . |
| 5,728,044 * | 3/1998 | Shan ................................. 600/117 |
| 5,729,129 | 3/1998 | Acker . |

FOREIGN PATENT DOCUMENTS

| | | |
|---|---|---|
| WO 95/07657 | 3/1995 | (WO) . |
| WO 95/09562 | 4/1995 | (WO) . |
| WO 95/10226 | 4/1995 | (WO) . |
| WO 95/19738 | 7/1995 | (WO) . |
| WO 96/05768 | 2/1996 | (WO) . |
| WO 96/41119 | 12/1996 | (WO) . |
| WO 97/03609 | 2/1997 | (WO) . |
| WO 97/29678 | 8/1997 | (WO) . |
| WO 97/29679 | 8/1997 | (WO) . |
| WO 97/29683 | 8/1997 | (WO) . |
| WO 97/29684 | 8/1997 | (WO) . |
| WO 97/29685 | 8/1997 | (WO) . |
| WO 97/29701 | 8/1997 | (WO) . |
| WO 97/29709 | 8/1997 | (WO) . |
| WO 97/29710 | 8/1997 | (WO) . |
| WO 97/29803 | 8/1997 | (WO) . |
| WO 97/32179 | 9/1997 | (WO) . |

\* cited by examiner

ATTACHMENT WITH ONE OR MORE SENSORS FOR PRECISE POSITION DETERMINATION OF ENDOSCOPES

RELATED APPLICATIONS this application is related to U.S. provisional application Ser. No. 60/011,743, titled "Pointing Device Packages", filed on Feb. 15, 1996 and 60/012,242, titled "Open-Lumen Passive Position Sensor", filed on Feb. 26, 1996, the disclosures of which are incorporated herein by reference. This application is also related to the following PCT applications filed on even date as the instant application by applicant Biosense Inc.: A PCT application titled "Locatable Biopsy Needle", filed in the Israeli receiving office, a PCT application titled "Catheter with Lumen" and a PCT application titled "Medical Probes with Field Transducers", both filed in the U.S. receiving office, the disclosures of all of which are incorporated herein by reference. This application is a CIP of PCT application Ser. No. PCT/IL97/00010, titled "Cardiac Electro-Mechanics" and filed in the Israeli receiving office by applicant Biosense LTD, on Jan. 8, 1997, the disclosure of which is incorporated herein by reference. The above PCT applications designate, inter alia, the U.S.

FIELD OF THE INVENTION

The present invention relates generally to the field of endoscopy, and specifically to endoscope assemblies with position sensors.

BACKGROUND OF THE INVENTION

The use of endoscopes for diagnostic and therapeutic indications is rapidly expanding. There are now many types of specialized endoscopes, such as endoscopes for the upper esophagus, stomach, and duodenum; angioscopes for blood vessels; bronchoscopes for the bronchi; arthroscopes for joint spaces; colonscopes for the colon; and laparoscopes for the peritoneal cavity. The present invention applies to all types of endoscopes.

Typically, endoscopes have a long and flexible insertion tube with a diameter ranging between 15–25 millimeters. The insertion tube is inserted into a patient's body, along a selected path, during an endoscopic procedure. Multiple work channels usually extend along the length of the endoscope within the insertion tube. The work channels may allow inserting biopsy tools into and taking biopsies from the patient's body. Other mechanisms, which may be incorporated in the endoscope, are a visual imaging device, an illumination device, and a deflection mechanism. The proximal end of the endoscope usually has a handle in which the controls of the endoscope residue. Ordinarily, endoscopes are made of metallic, electrically conducting, materials. For example, U.S. Pat. No. 4,869,238 whose disclosure is incorporated herein by reference, describes a standard three-layer wall for endoscopes, containing metal coils and wire mesh.

Cleaning and sterilizing endoscopes are expensive and tedious procedures. Endoscopes incorporate expensive and delicate apparatus which may be damaged during cleaning. Also, the long and narrow work channels in the insertion tube are difficult to clean.

Disposable endoscopic sheaths have been developed, to avoid the need for cleaning and sterilizing endoscopes. These sheaths substantially isolate the endoscope from the patient, and thus prevent the endoscope from being contaminated. Some of these sheaths have thick walls containing work channels within them, leaving only part of their cross-section for a lumen which receives the insertion tube of the endoscope. The walls of the work channels and the area between the work channels usually comprise the same material as the outer wall.

A sheath with thick walls is described, for example, in PCT publication WO 94/287282, whose disclosure is incorporated herein by reference. WO 94/28782 describes a disposable sheath which may include work channels. The sheath removably receives a cylindrical insertion tube which contains controls and other delicate apparatus of the endoscope. Another disposable sheath is described in U.S. Pat. No. 5,483,951, whose disclosure is incorporated herein by reference. This disposable sheath comprises a thin outer wall, inner work channels, and a lumen with a "D" shaped cross-section. The lumen is adapted to receive and substantially isolate a non-disposable insertion tube of an endoscope, which is accordingly "D" shaped.

many endoscopic procedures involve irreversible actions such as taking tissue samples and ablation at the distal end of the insertion tube of the endoscope. Performing these actions at an incorrect position can damage important blood vessels or nerves, puncture the intestine, or otherwise cause severe damage to the patient. Therefore it is useful to have a method of determining the position and/or orientation of the distal end of the endoscope.

Through a visual imaging device the user can observe images transmitted from the distal end of the endoscope. From these images and from knowledge of the path the endoscope has followed, the user can ordinarily determined the position of the endoscope. However, there are organs of the human body in which the images and knowledge of the path do not suffice to determine the position of the endoscope to sufficient accuracy. Some organs, such as the brain, have a homogeneous appearance in which it is very hard or even impossible to find a specific point based only on the images from the imaging device. In addition, determining the position of he endoscope from the images could be very time consuming. In many endoscopic procedures, such as endoscopic bypass surgery, the amount of the time a patient can endure the endoscopic procedure is limited.

In some procedures, the endoscope is used to map a section of an organ. The map is produced by systematically bringing the distal end of the endoscope in contact with a plurality of points within the organ and registering the positions of the points. To confirm that the entire section of the organ has been mapped, a sufficient density of points must be registered within the section. To insure use of a sufficient density of points it is necessary to have unique position identification for every point.

Another problem which arises, for example, in colonscope procedures, is formation of loops in the long and narrow tube of the colonscope. Such loops may arise when the insertion tube encounters an obstacle, or gets stuck in a narrow passage. Instead of progressing, the tube forms loops within the patient. In an attempt to proceed in insertion of the colonscope, excess force may be exerted, damaging delicate tissue in the patient's body. The user may proceed with the attempted insertion of the endoscope without realizing there is a problem. The ability to see the configuration of the endoscopic insertion tube within the patient's body, allows early discovery of the existence of loops and makes straightening them simpler.

One method used in the art of determine the configuration of the insertion tube is x-ray imaging. Another method used is magnetic field positioning, which avoids the x-ray exposure to the patient and the operator. PCT application PCT/

GB93/01736, whose disclosure is incorporated herein by reference, describes a method of magnetic filed position determination using low frequency magnetic fields to determine the position of a miniature sensor embedded within a colonscope tube. Based on the position of the sensor at sequential time periods, an image of the configuration of the colonscope tube is produced.

In tests mentioned in PCT/GB93/01736 it was found that there were some distortions in the image due to the metallic construction of the colonscope. The metallic construction of the colonscope reacts with the sensing magnetic filed in that currents are induced in the colonscope by the magnetic filed. These currents, called eddy currents, generate a disturbing magnetic field which is overlaid on the sensing magnetic field. Thus, the amplitude and/or phase of the magnetic field used by the position determining system are changed in proximity of metallic substances. The magnitude and effect of the eddy currents depend on the size and geometry of the metallic substance. For example, large metal rings change the magnetic field substantially in their proximity. Conversely, small metal objects and objects with a relatively high resistance, within which substantially no eddy currents are formed, does not substantially affect the magnetic field.

Magnetic filed position determining systems typically determine positions according to the magnetic filed's amplitude and/or its phase. Changes in the amplitude and/or phase due to eddy currents cause inaccuracies in determined positions and interfere with precise determination of positions. Interference can also arise from ferro-magnetic materials in the endoscope, which concentrate the magnetic filed in their proximity. Thus, ferro-magnetic materials cause distortions in the magnetic field, changing the amplitude and phase of the field at measured points.

The interference is dependent on the frequency of a drive signal which generates the magnetic field. A high drive signal frequency is preferred in order to enhance sensor sensitivity, but must be limited so as not to intensify the interference to the position determining system. Therefore, the PCT/GB93/10736 system makes a compromise in its choice of the frequency used. If a different method to minimize the interference is used, it would be possible to enjoy the advantages of a higher drive signal frequency.

Existing catheters have a metal coil (for structural purposes) within them. The coil extends along the length of the catheter except for a small part of the distal end of the catheter. A sensor coupled with a magnetic filed position determining system is embedded within the distal end of the catheter.

SUMMARY OF THE INVENTION

It is an object of some aspects of the present invention to provide accurate positioning of an endoscope using a magnetic field position determining system.

It is further object of some aspects of the present invention to provide an endoscopic sheath which, when it receives an insertion tube of an endoscope, allows accurate position determination of points within the insertion tube.

Another object of some aspects of the present invention is to distance one or more position sensors, embedded at any point along an insertion tube of an endoscope, from materials, structures and signal sources within the endoscope which may interfere with position determination. Such materials, structures and signals sources are referred to herein as "interference causing structures".

In some preferred embodiments of the invention, the position determining system uses magnetic fields to determine positions. In these embodiments the interference causing structures usually consist of electrically conducting and/or ferro=magnetic materials. The interference causing structures could be in any of various components of the endoscope, such as control wires, metal coils, reinforcements of the endoscope's walls, electric wires, etc. The interference is dependent on the size and geometry of the interference causing structures, and on the distance between the sensors and the interference causing structures substance. More specifically, the interference is approximately inversely proportional to the cube of the distance between the sensors and the interference causing structures. When using an amplitude-based position determining system, a distance between 1 3 mm is typically sufficient to reduce the interference to less than 1% of the field used by the position determining system.

In accordance with preferred embodiments of the invention, an endoscopic sheath preferably comprises only non-interference causing structures. Preferably, the walls of the endoscopic sheath contain, within them, work channels and therefore are thick. Preferably, the sheath comprises a lumen which receives the insertion tube of an endoscope. One or more sensors are embedded within the sheath, preferably in regions farthest from the lumen. Thus, when the insertion tube is placed in the lumen, the sensors are distanced from the interference causing structures. The insertion tube is, preferably, tightly and precisely positioned within the sheath so that positions of points within the insertion tube are easily determined relative to the sensors.

In further embodiments of the present invention, the distal end of the sheath extends beyond the insertion tube and isolates the tip of the insertion tube from the patient's body. In some sheaths of the invention the distal end comprises a transparent window allowing the distal end of the endoscope a clear view. Preferably, the distal end of the sheath comprises substantially no interference causing structures. A sensor is embedded within the distal end of the sheath away from interference causing structures which are within the insertion tube. Preferably, the sensor does not obscure the view through the transparent window. Thus, when inserting the insertion tube into the sheath a sensor is situated at the tip of the endoscope with substantially not interference causing structures in it proximity. This is true even if the tip of the insertion tube is comprised of interference causing structures.

It is noted that, in some prior art sheaths, there are some metal components within the sheath. In accordance with preferred embodiments of the present invention, in these sheaths, the sensors are preferably embedded at points at which the interference is minimal when the insertion tube is within the sheath. Preferably, tests are performed during a design stage to find these points. In these tests, performed when the insertion tube is within the sheath, the interference induced by the interference causing structures is measured, and the positions of the sensors are chosen accordingly. In this embodiment it is important to identify the preferred orientation of the insertion tube within the sheath, in order that the interference to the sensors will be the same as at the time of the tests.

Israeli Patent Application No. 119,262, filed by Biosense Ltd. on Sep. 17, 1996, which is assigned to the assignee of the present invention, and is incorporated herein by reference, describes a sheath having an embedded position sensor suitable for a disposable biopsy needle. In accordance with a preferred embodiment of the present invention the biopsy needle is made of a non interference causing substance, such as carbon, so that the structure of the biopsy needle does not interfere with the operation of the position determining system. Alternatively, the sheath is thick enough to distance the sensor from the biopsy needle. Israeli Patent Application No. 117,148, titled "Catheter with a Lumne", filed by Biosense LTD. on Feb. 15, 1996, the disclosure of which is incorporated herein by reference, describes catheters having a large lumen and a position sensor which does not block the lumen during its operation.

In another preferred embodiments of the invention, one or more position sensors are embedded within a sheath which covers an invasive tool. In an exemplary embodiment of the invention the invasive tool is a pacemaker electrode, which is usually inserted by guiding the electrode through a vein into the right atrium, and then, the right ventricle, where the electrode is fixed at the apex using a screw, clip or other type of suture. Knowledge of the exact location of attachment of the electrode is desirable for various reasons, in particular those described in a PCT application filed in the Israeli Receiving office on Jan. 8, 1997 and title "Cardiac Electro-Mechanics" to inventors Shlomo Ben-Haim and Maier Fenster, the disclosure of which is incorporated herein by reference. This PCT application describes various methods of determining the activation profile of the heart and, based on that profile and/or an electrical activation map and/or a mechanical activation map of the heart, determining an optimal location for such a pacemaker electrode. One aim is to avoid attaching the electrode to diseased tissue (which will increase the drain on the pacemaker power supply and/or hurt the patient). Another aim is to achieve a particular activation profile of the heart using the pacemaker electrode. The position sensor assists in guiding the insertion of the pacemaker electrode to a required position in the patient's heart. After the pacemaker electrode is attached at it required position the sheath is peeled off of the pacemaker electrode and taken out of the patient's body along with the sensors. In a preferred embodiment of the invention, the sheath includes a steering mechanism, as known in the art, to deflect the electrode while navigating through blood vessels and in the heart, towards a desirable attachment location. It should be appreciated that since pacemaker electrodes are usually inside the patient's heart and flex with each heart beat, the probability of some foreign material breaking off the electrodes is great, as is the possible damage to the patient. Pacemaker electrodes are typically specially engineered to resist corrosion and breakage under this type of constant strain, while it is not desirable to apply the same engineering principles to position sensors, due to considerations of cost and to technological limitations. This embodiment of the invention is also especially useful with other invasive tools, such as infusion tubes, which remain in the patient's body for long periods.

In some preferred embodiments of the present invention, the sensors are not embedded within a sheath. Rather, the sensors are embedded within attachments which are affixed to the endoscope. These attachments are of substances which are substantially not interference causing to the operation of the position determining system, and a preferably thick enough so as to form an effective separation between the sensors and interference causing structures within the endoscope. The attachments may be attached to the endoscope using an adhesive, or by any other connection method. In some embodiments of the invention a sheath is used to cover both the endoscope and the attachments thereon. The sheath isolates the endoscope from the surroundings and also keeps the attachments, and sensors, fixed to the endoscope. In a preferred embodiment one long attachment is laid along the length of the endoscope, and within it are one or more sensors.

In further preferred embodiments of the present invention, separation of the sensors from the interference causing structures is achieved without using a separate disposable part. Rather, the insertion tube itself is partitioned, forming regions free of substances interference causing to the operation of position determining systems. Within these regions one or more sensors are embedded, distanced for the interference causing structures. Thus, the sensors and the interference causing structures are separated, substantially eliminating interference to the operation of the position determining system.

In some preferred embodiments of the present invention, a widthwise separation is employed. In widthwise separations the regions free of interference causing structures are located at predetermined regions of the cross-section of the insertion tube. In one preferred embodiment of the invention, the separation is such that interference causing structures are axially centered, and regions adjacent the circumference are free of interference causing structures. Thus, most parts of these regions are substantially free of interference, if the diameter of the sheath is large enough. In another preferred embodiment of the invention, the interference causing structures are confined to a "D" shaped area of the ordinarily circular cross-section of the endoscope. Thus, the rest of the cross-section is free of interference causing structures, and therefore a major part of the cross-section is substantially free of interference.

In one preferred embodiment of the invention based on a lengthwise separation, one or more sections along the length of the insertion tube are substantially free of interference causing structures. In another embodiment of the invention, interference causing structures run along the entire length of the insertion tube. However, there are one or more segments along the length of the insertion tube in which the interference causing structures are confined to a part of the cross-section. Thus, some regions of the cross-section of these segments are free of interference causing structures. Accordingly, the sensors of the position determining system are embedded within these regions at points which are substantially free of interference.

Preferably, these points are the points in the insertion tube with the least interference. Preferably, these points are chosen according to tests as described above regarding previous embodiment of the invention. Alternatively, the sensors are embedded at points substantially farthest from all interference causing structures within the insertion tube.

There is therefore provided in accordance with a preferred embodiment of the invention, a locatable endoscope attachment connectable to an endoscope for determining the endoscope's position; and one or more sensors, fixedly positioned with respect to the attachment, which are used for determining the positions of the one or more sensors.

Preferably when the attachment is fixedly attached to the endoscope, the one or more sensors are distanced from elements of the endoscope which interferes with determining the positions of the one or more sensors.

Preferably the one ore more sensors are embedded within the attachment.

Preferably the attachment does not contain elements which substantially interfere with the determining of positions of the one or more sensors.

In a preferred embodiment of the invention determining the positions of the one or more sensors is performed by transmitting and receiving magnetic fields.

Preferably there are markings on the outside of the attachment which indicate the positions of the one or more sensors.

In a preferred embodiment of the invention the attachment includes a tube.

There is further provided, the in accordance with a preferred embodiment of the invention, an endoscopic positioning and sensing kit including one or more attachments as described above; and a thin sheath which covers the endoscope and the one or more attachments.

In a preferred embodiment of the invention the attachment includes a sheath which has a lumen and a circumference, preferably the lumen has a "D" shaped cross-section and the one or more sensors are spaced from materials which interfere with the determining of positions, by an amount sufficient to substantially avoid the interfering effect of the materials.

Alternatively, or additionally, the lumen is axially centered within the sheath, and the one or more sensors are positioned adjacent the circumference of the sheath.

Preferably, the sheath has a distal end which extends beyond the lumen and at least one of the one or more sensors is embedded within the distal end.

There is further provided, in accordance with a preferred embodiment of the invention, a locatable endoscope including an insertion tube having an elongate body with a cross-section, a circumference, and a tip; and one or more sensors positioned at fixed points of the body, preferably the one or more sensors are used for determining the positions of the one or more sensors, and portions of the cross-section of the elongate body, distal from the tip and adjacent the one or more sensors, do not contain substances which substantially interfere with determining the positions of the one or more sensors.

Preferably, the one or more sensors are positioned at points of the cross-section of the elongate body where elements of the insertion tube which interfere with determining the positions of the one or more sensors have the last effect.

Preferably, the one or more sensors are embedded within the insertion tube.

Preferably, determining the positions of the one or more sensors is performed by transmitting and receiving magnetic fields.

Preferably, the one or more sensors are positioned at points within the insertion tube substantially farthest from electrically conducting and ferro-magnetic materials.

Preferably, the substances which interfere with determining the positions of the one or more sensors are confined to a "D" shaped cross-section of the elongate body, and the one or more sensors are distanced from materials which interfere with the determining of positions, by an amount sufficient to substantially avoid the interfering effect of the materials.

Alternatively the substances which interfere with determining the positions of the one or more sensors are confined to a round, axially centered, cross-section of the elongate body; and the one or more sensors are positioned adjacent the circumference of the insertion tube.

The present invention will be more fully understood from the following detailed description of the preferred embodiments thereof, taken together with the drawings, in which:

DETAILED DESCRIPTION OF PREFERRED EMBODIMENTS

Figures 1, 2:
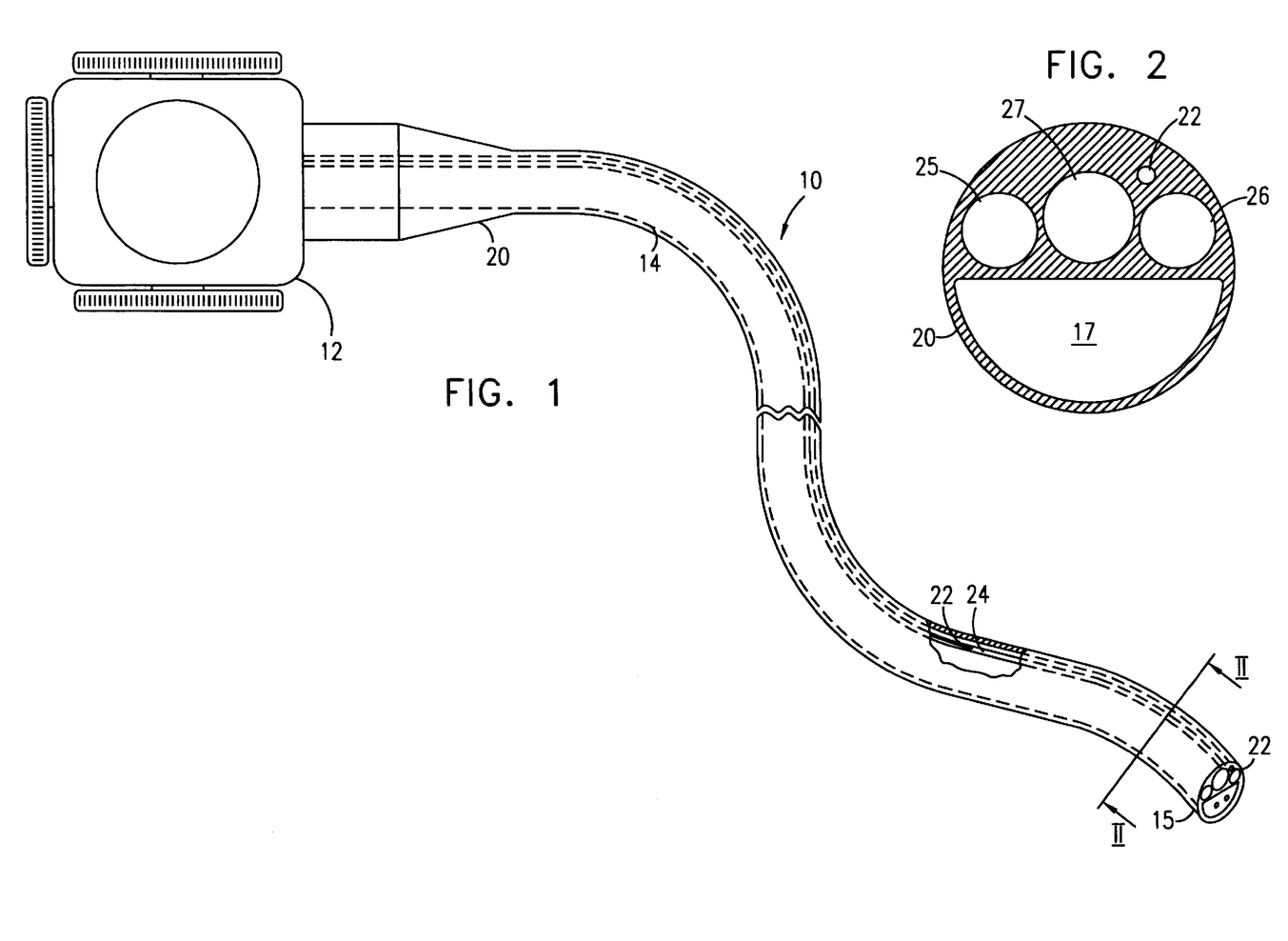
FIG. 1 is a perspective view of an endoscopic sheath installed over a colonscope, in accordance with a preferred embodiment of the present invention.
FIG. 2 is an enlarged cross-sectional view of the endoscopic sheath of FIG. 1, taken along line II—II toward the distal end of the endoscopic sheath, not showing the colonscope's insertion tube.

Reference is made to FIG. 1 which shows a flexible endoscopic sheath 20, installed over an endoscopic insertion tube 14 of a colonscope. Colonscope 10, comprising a control unit 12 and insertion tub 14 which as a distal end 15. Colonscope 10 is placed in a flexible endoscopic sheath 20, which is adapted to tightly receive tube 14. Insertion tube 14 and sheath 20 are inserted together into a patient's body, such that tube 14 is essentially isolated from the patient's body. One or more sensors 22 are embedded along sheath 20 as described below. A position determining system (not shown) determined the position in space of sensors 22, preferably, according to magnetic fields transmitted to and/ or from sensors 22.

Insertion tube 14 is a long and narrow flexible tube with durable walls, and preferably has a "D" shaped cross-section. A deflection mechanism, a visual imaging device, and possible other apparatus are located within the tube 14. Wires serving the apparatus within the colonscope, run along insertion tube 14 from its distal end 15 to control unit 12. Ordinarily, tube 14 is a non-disposable elongate tube, which comprises electrical conducting materials.

Flexible endoscopic sheath 20 is an elongate disposable tube which generally comprises materials which do not interfere with the operation of the position determining system. Interfering materials include electrically conducting materials, and ferro-magnetic materials. Preferably, sheath 20 comprises polyethylene or polyvinylchloride ("PVC"), but can comprise any durable lubricious material. It is noted that in some prior art descriptions sheath 20 also comprises a metal spring or other electrically conducting part. In the present invention, where such sheath are used, measurements are preferably made, in the design stage, to determine the interference induced by the conducting part. The influence of the conducting part of the sheath may be ignored if the interference it induces is small relative to the interference induced by materials within the colonscope. Alternatively, in accordance with the present invention, a similar sheath may be used in which the conducting part is replaced by a functionally equivalent part, comprising non-conducting material.

As can best be seen in FIG. 2, which is a cross-sectional view of endoscopic sheath 20 of FIG. 1, without the colonscope's insertion tube, sheath 20 preferably has a circular external cross-section. Within sheath 20 there is a lumen 17, shaped and sized to tightly receive insertion tube 14. The rest of the cross-section of sheath 20 contains several work channels 25, 26 and 27 running substantially parallel to the longitudinal axis of sheath 20. Work channels 25, 26 and 27 are used to pass materials and apparatus in and out of the patient's body, such materials as air, water and also biopsy taking apparatus. In an exemplary embodiment channel 25 is an air channel, channel 26 is a water channel, and channel 27 is used for passing biopsy taking apparatus into the patient and is called a biopsy channel. It is noted that occasionally, electrically conducting apparatus, which induces interference, is passed through biopsy channel 27. Ordinarily, substantially no interference to the operation of the position determining system is caused by such apparatus, because of the small size of the apparatus, and the distance between the apparatus and sensors 22. However, preferably, work channels near sensors 22 are allocated tasks which do not include passing interfering materials through them. Accordingly, sensors 22 are embedded farthest from biopsy channel 27. In other words, the channel farthest from sensors 22 is used for biopsy apparatus.

As mentioned above, along sheath 20 there are one or more miniature sensors 22, which are used in conjunction with the position determining system. In a preferred embodiment of the invention the sensors sense the amplitude and/or phase of the magnetic field in their proximity. The position determining system uses the amplitude and/or phase to determine positions within the endoscope. Each of sensors 22 measures at least three coordinates. Preferably, each sensor 22 allows determination of the six coordinates of position and orientation. Alternatively, a few sensors which measure only two coordinates, may be used, if the sensors are fixedly positioned relative to each other. The sensors are, preferably, miniature coils such as described, for example, in PCT/GB93/01736, U.S. Pat. No. 5,391,199, PCT publication WO95/04938, PCT publication WO96/05768, or U.S. Provisional patent application No. 60/011,724, filed Feb. 15, 1996, which is assigned to the assignee of the present application, all of which patents, publications and applications are incorporated herein by reference. Sensors 22 are located on the inner side of sheath 20 near its circumference, spaced from interfering materials by an amount sufficient to avoid interference to the operation of the position determining system. In a preferred embodiment of the invention, the sensors are diametrically opposite lumen 17. As can best be seen in FIG. 1, wires 24, running along sheath 20, connect sensors 22 to the position determining system (not shown). Wires 24 are then enough so as to take up minimal space of the interior of sheath 20, and also so as not to interfere with the operation of the position determining system. Alternatively, sensors 22 are wireless. In a preferred embodiment of the invention, at least one sensor 22 is coupled with a transmitter on an integrated circuit.

Before insertion of tube 14 into a patient, it is tightly placed and precisely oriented within sheath 20. In addition, distal end 15 of tube 14 is preferably brought to a re-locatable depth within sheath 20. Thus, precise positional co-ordination between sensors 22 and insertion tube 14, is achieved.

One method of tightly attaching a sheath to an endoscope is to shrink the sheath around the endoscope using chemical or heat methods. Preferably, such a sheath includes a "rip cord", such as a Kevlar® cable running along the inside of the sheath, to facilitate removal of the sheath after usage. Pulling such a rip cord, perpendicular to the endoscope, rips the sheath so that is may be easily removed from the endoscope. Such a cord is especially important if the cross-section of the endoscope is not constant, such as due to attachments.

Sensors 22 are precisely fixed, relative to sheath 20 and hence to insertion tube 14, so that the position determining system will be able to determine the position of any point along sheath 20 and insertion tube 14. In addition, sensors 22 are preferably embedded within sheath 20 to protect sensors 22 from the surroundings.

In some preferred embodiments of the invention the position determining system uses DC currents. In these embodiments, conducting materials do not interfere with the operation of the position determining system. Therefore the sensors are distanced only from ferro-magnetic materials. In these systems, the decision of where to place the sensors is performed according to the locations of ferro-magnetic materials within the insertion tube.

Figure 3:
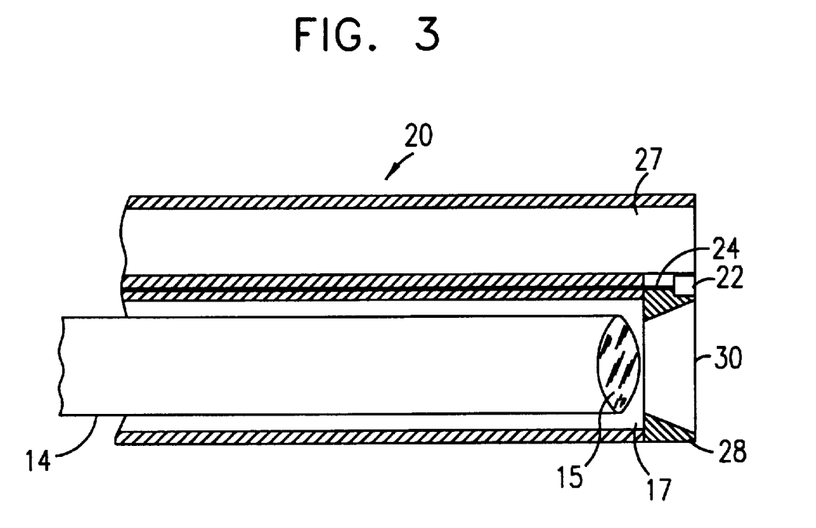
FIG. 3 is a side cross-sectional view of a further preferred embodiment of the present invention.

Reference is now made to FIG. 3 which shows an endoscopic sheath in accordance with a preferred embodiment of the present invention. In some embodiments of the present invention, sheath 20 has a distal end 28 which extends beyond distal end 15 of tube 14. Distal end 28 preferably isolates distal end 15 from the patient's body. Sheath 20 preferably has a transparent window 30 on its distal end 28, allowing an imaging device within tube 14 an unobstructed field of view. Window 30 preferably comprises a clear transparent optical grade plastic, as described, for example, in U.S. Pat. No. 5,402,768, which is incorporated herein by reference. In accordance with the present invention, distal end 28 is substantially free of substances interference causing to the operation of the position determining system. Therefore, substantially no interference is induced on a sensor 22 embedded within distal end 28. Preferably, distal end 28 is thick enough to contain at least one sensor 22 in such a way that does not obscure the view thorough window 30. In a preferred embodiment of the present invention, the interference to the position determining system at different points within distal end 28 is measured, and sensor 22 is embedded at a point which has the least interference.

Figure 4:
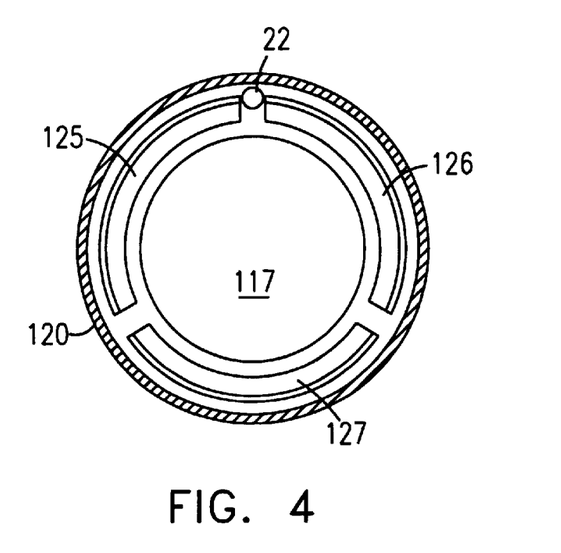
FIG. 4 is a cross-sectional view of another preferred embodiment of the present invention.

Reference is made to FIG. 4 which shows the cross-section of a sheath 120 in accordance with another embodiment of the invention. Sheath 120 comprises a cylindrical lumen 117 which is preferably, axially centered within sheath 120. Lumen 117 is shaped to tightly receive an endoscopic insertion tube. Several work channels run parallel to lumen 117, within sheath 120, radially surrounding lumen 117. Preferably, there are three channels, for example, for air 125, for water 126 and for biopsy apparatus 127. One or more sensors 22 are embedded along sheath 120, preferably, on the outer circumference of sheath 120, as far as possible from lumen 117. Preferably, sensors 22 are embedded near air channel 125, and water channel 126, so as to keep them away from any metal apparatus passing through biopsy channel 127.

On the insertion tube, there is preferably a marking indicating the correct orientation of the insertion tube within the lumen. In a preferred embodiment of the invention, the insertion tube has a key, and the lumen has corresponding slot. Thus, the insertion tube can be inserted into the lumen only in the correct orientation. In addition, the distal end of the insertion tube contacts the inner surface of the distal end of the lumen. Thus, the position determining system can precisely register the location and orientation of the insertion tube according to the position of sensors 22.

Figures 5, 6:
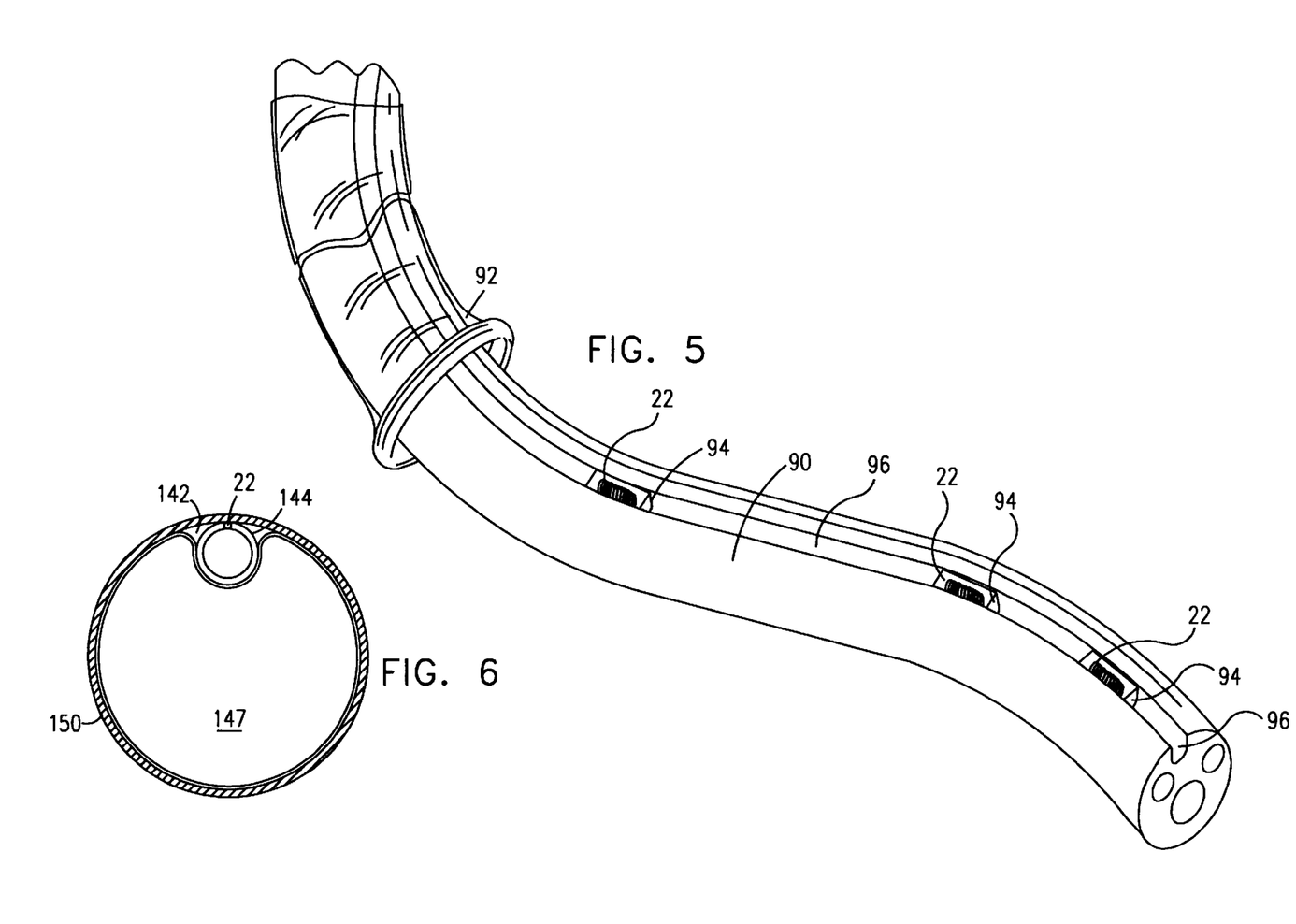
FIG. 5 is a perspective view of an endoscope with sensor attachments in accordance with a preferred embodiment of the present invention.
FIG. 6 is a cross-sectional view of yet another preferred embodiment of the present invention.

In some preferred embodiments of the present invention, the sensors are embedded within attachments to the endoscope. Reference is now made to FIG. 5 which shows an endoscope with sensors in accordance with a preferred embodiment of the invention. As shown in FIG. 5, and endoscope 90 has one or more attachments 94 which incorporate sensors 22. Preferably, endoscope 90 has a groove 96 along at least part of its length. Attachment 94 are, preferably, situated within groove 96 and are preferably shaped to smoothly fit in groove 96 without protruding from it. Attachments 94 are comprised substantially of non-interference causing materials and are preferably thick enough so as to substantially separate between sensors 22 and interference causing structures within the endoscope. Preferably, an adhesive connects attachments 94 to endoscope 90. Alternatively, or additionally, attachments 94 are connected to endoscope 90 using any connection method known in the art. Sensor 22 are preferably embedded within attachments 94 in the portion of attachment 94 farthest from endoscope 90. Thus, most of each attachment 94 separates its associated sensor 22 from interference causing structures within endoscope 90.

In a preferred embodiment of the invention, a thin sheath 92 covers endoscope 90 and attachments 94, and thus isolates endoscope 90 from the patient's body and also keeps attachment 94 in fixed positions on endoscope 94. Before insertion of endoscope 90 into the patient, endoscope 90 is preferably brought to an external reference calibration point and the position determining system registers the positions of the sensors relative to endoscope 90.

In a preferred embodiment of the invention, one or more sensors are situated within one long attachment which is placed along the endoscope. Reference is now made to FIG. 6, which shows a cross-section of an endoscopic assembly, in accordance with another embodiment of the present invention. As shown in FIG. 6, a disposable sheath 150 isolates an endoscope 147 from the patient's body. A groove 142 runs along the length of endoscope 147. A disposable tube 144 is laid along endoscope 147 within groove 142, such that sheath 150 covers endoscope 147 and tube 144. Endoscope 147 and tube 144 can be, for example, as described in U.S. Pat. No. 4,646,722, whose disclosure is incorporated herein by reference. In accordance with the present invention, one or more sensors 22 are fixed along disposable tube 144, and preferably are embedded within its wall. Sensors 22 are embedded substantially along a straight line parallel to the longitudinal axis of tube 144. On the outer side of tube 144, this straight line is preferably marked to identify where sensors 22 are embedded. The marking helps the user lay tube 144 in groove 142 such that sensors 22 are adjacent to sheath 150, and therefore are distanced from interference causing structures within endoscope 147. Also, the position of the sensors in relation to endoscope 147 is thus accurately established.

It is noted, that although in the above embodiments the sheath is separate from the insertion tube of the endoscope, the sheath can also be a non-separable part of the insertion tube. In such embodiments, there is no separable sheath, but rather there is one endoscopic insertion tube with two parts. One part contains the circumference of the insertion tube and the work channels and is substantially free of interference causing structures, and the other part is the core of the insertion tube which contains interference causing structures. In accordance with preferred embodiments of the invention, the sensors are embedded in the part which is free of interference causing structures.

Figure 7:
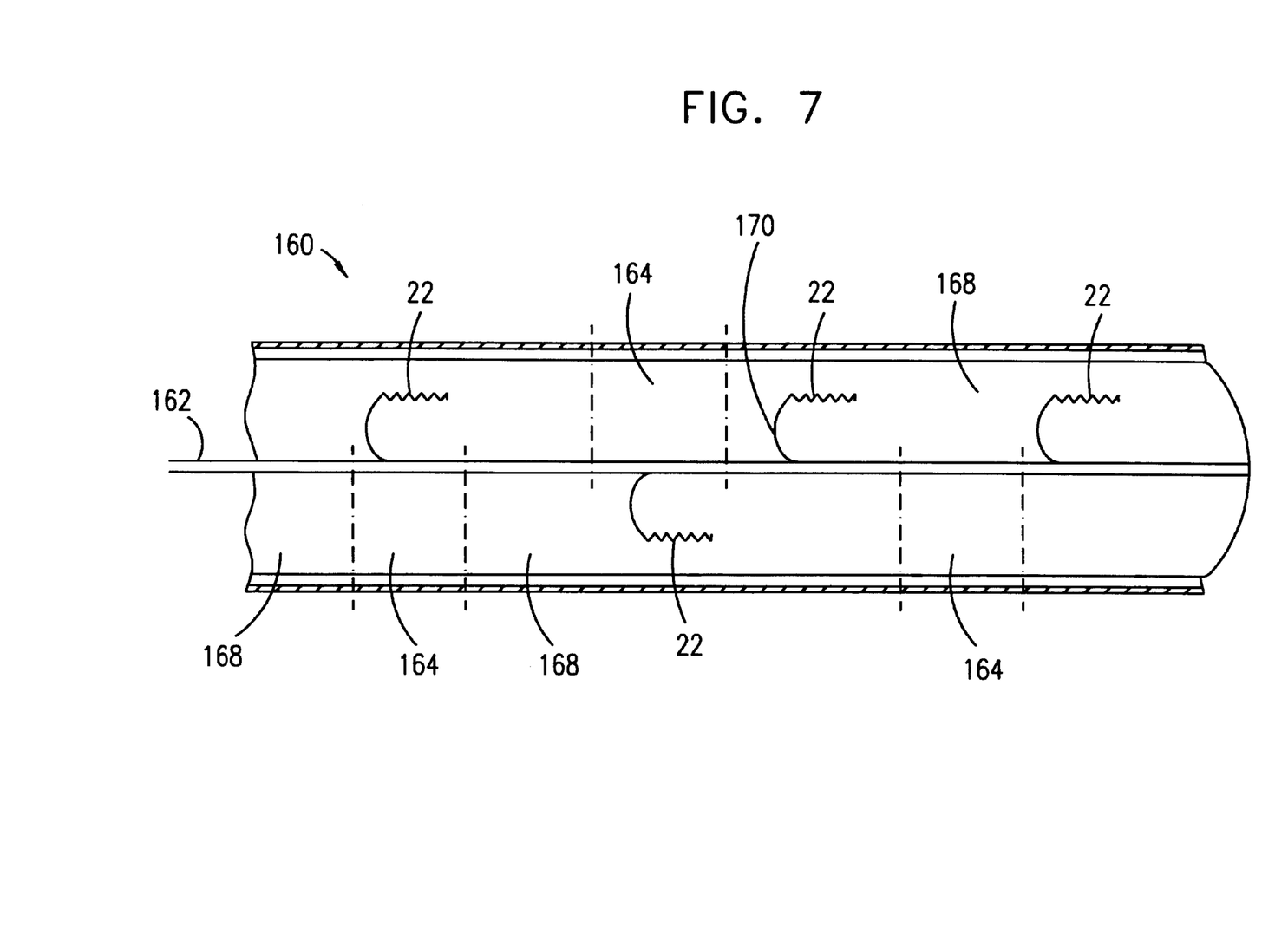
FIG. 7 is a side cross-sectional view of an endoscope in accordance with another preferred embodiment of the invention.

Reference is now made to FIG. 7 which shows an endoscopic insertion tube 160 with a combined lengthwise and widthwise division in accordance with a preferred embodiment of the invention. As shown in FIG. 7, insertion tube 160 has an axial metal core 162, and sections 164 which contain various apparatus of insertion tube 160. The apparatus in sections 164 are parts of a deflections system or other systems such as a visual imaging system, and contain interference causing structures. Other sections 168, which do not contain interference causing structures, have embedded within them one or more sensors 22. Axial core 162 is preferably thin and contains wires which connect the device within insertion tube 160 with the proximal end of insertion tube 160. Preferably, also wires 170, which connect sensors 22 to a position determining system outside of the endoscope, run within axial core 162.

It is noted, that although the invention has been described in conjunction with a magnetic field position determining system, it can also be used with other position determining systems, such as, acoustic position determining systems. When using acoustic position determining, hard substances within the insertion tube reflect acoustic waves and therefore interfere with the operation determining positions. Therefore, in accordance with the present invention, the sensors, which are ordinarily transducers, are distanced from hard substances within the insertion tube. The distancing is performed in a manner similar to the described above distancing of magnetic field sensors from conducting and ferro-magnetic materials.

It is also noted, that although the invention has been described in conjunction with an endoscope, it can also be used with any other medical instrument for which position determination is desired. In particular, the invention can be used with invasive tools such as catheters and feeding tubes.

It will be appreciated that the preferred embodiments described above are cited by way of example, and the full scope of the invention is limited only by the claims.

What is claimed is:

1. A locatable endoscope attachment for an insertion tube portion of an endoscope having interfering elements comprising:

an attachment connectable to an insertion tube portion of an endoscope for determining the endoscope's position;

one or more sensors, fixedly positioned with respect to the attachment, which are used for determining the positions of the one or more sensors, wherein the attachment is fixedly attached to the endoscope and the one or more sensors are distanced from the interfering elements of the endoscope, the one or more sensors being embedded within the attachment, wherein the one or more sensors transmit or receive magnetic fields; and a plurality of markings on the outside of the attachment which indicate the positions of the one or more sensors.

2. The attachment of claim 1, wherein the attachment comprises a tube.

3. A position determining system for an endoscope having interfering elements comprising:

an attachment connectable to a position of an endoscope;

at least one sensor within said attachment distanced from the interfering elements of the endoscope, said at least one sensor for transmitting or receiving magnetic fields;

a plurality of markings on the outside of the attachment which indicate the position of the at least one sensor; and a sheath for covering said attachment.

4. The position determining system of claim 3 including an endoscope.

* * * * *